United States Patent [19]

Schwinn et al.

[11] Patent Number: 4,670,544

[45] Date of Patent: Jun. 2, 1987

[54] PROCESS FOR THE MANUFACTURE OF THE COLD INSOLUBLE GLOBULIN AND PHARMACEUTICAL PREPARATION CONTAINING IT

[75] Inventors: Horst Schwinn; Norbert Heimburger, both of Marburg an der Lahn; Gerhard Kumpe, Wetter; Bernd Herchenhan, Kirchhain, all of Fed. Rep. of Germany

[73] Assignee: Hoechst Aktiengesellschaft, Frankfurt am Main, Fed. Rep. of Germany

[21] Appl. No.: 871,211

[22] Filed: Oct. 11, 1983

Related U.S. Application Data

[63] Continuation of Ser. No. 435,507, Oct. 19, 1982, abandoned, which is a continuation of Ser. No. 296,829, Aug. 27, 1981, abandoned, which is a continuation of Ser. No. 92,193, Nov. 7, 1979, abandoned.

[30] Foreign Application Priority Data

Nov. 9, 1978 [DE] Fed. Rep. of Germany ....... 2848529

[51] Int. Cl.[4] .......................... A61K 35/14; C07K 3/24

[52] U.S. Cl. .................................. 530/392; 424/101; 530/386; 530/830; 514/21

[58] Field of Search ...................... 530/386, 392, 830; 424/101; 514/21

[56] References Cited

U.S. PATENT DOCUMENTS

| 3,631,018 | 12/1971 | Shanbrom ...................... 530/830 X |
| 4,315,906 | 2/1982 | Geider ............................ 530/386 X |
| 4,424,206 | 1/1984 | Ohmura et al. ................. 530/386 X |
| 4,565,651 | 1/1986 | Ohmura et al. ..................... 530/392 |

OTHER PUBLICATIONS

J. Lab. Clin. Med. 67:23–32, Jan. 1966, Hershgold et al.
J. Biol. Chem. 245, No. 21, 5728–5736, Nov. 1970, Mosesson et al.
Lab. Manual of Analytical Methods of Protein Chemistry, vol. 1, 1960, Alexander et al.

*Primary Examiner*—Howard E. Schain
*Attorney, Agent, or Firm*—Curtis, Morris & Safford

[57] ABSTRACT

What is disclosed is a method for isolating the cold insoluble globulin (CIG) from blood plasma concentrates containing factor VIII.

3 Claims, No Drawings

PROCESS FOR THE MANUFACTURE OF THE COLD INSOLUBLE GLOBULIN AND PHARMACEUTICAL PREPARATION CONTAINING IT

This application is a continuation of application Ser. No. 435,507, filed Oct. 19, 1982 abandoned, which is a continuation of application Ser. No. 296,829, filed Aug. 27, 1981, which in turn is a continuation of application Ser. No. 92,193, filed Nov. 7, 1979 and now abandoned.

The present invention relates to a process for the manufacture of the cold insoluble globulin, in particular from factor VIII concentrates of blood plasma, and to a pharmaceutical preparation containing this globulin.

The cold insoluble globulin(CIG) has long been described in the literature as being a protein found in the plasma which is designated as "large external transformation-sensitive protein"=LETS, "soluble fibroblast antigen"=SF, "cell surface protein"=CSP, "cell adhesion factor"=CAF, or fibronectin, and as being a component of the surface of fibroblasts.

It is known that this protein is obtainable from the Cohn I-fraction or from the cryoprecipitate of ACD (Acidum citricum dextrose) plasma, in preparative amounts [Mosesson, M. W. and Umfleet, R. A., J. Biol. Chem. 245, 5728 (1970)]. The starting material is reported to contain, in addition to other cold insoluble trace proteins, mainly fibrinogen (80–85%) and the CIG (at most 10%).

The problem involved in CIG preparation is in the first place that of separating the CIG from the fibrinogen, whose precipitation and fractionation properties are very similar to those of the CIG. This has been tested by Mosesson (loc. cit.) by fractionation with glycine/ethanol at low temperatures.

However, the protein enriched in this way still contains approximately 50% of fibrinogen, a satisfactory removal of the latter being ensured only by a subsequent ion exchanger step.

It is further known that the commercially available factor VIII concentrates, substantially independent of their origin and methods of preparation, contain fibrinogen and CIG in relatively high concentrations and in varying ratios as accompanying proteins.

It has now been found that CIG can surprisingly be obtained in a high purity from CIG-containing factor VIII concentrates poor in fibrinogen in a few fractionation steps. Thereby, on the one hand, the CIG and, on the other hand, the factor VIII are available.

The present invention therefore relates to a process for the preparation of the cold insoluble globulin (CIG) from CIG-containing factor VIII concentrates, advantageously poor in fibrinogen, which comprises (a) adding from 1.8 to 2.6 mols/l of a well water-soluble aliphatic amino acid and of from 8 to 12 w/v % of neutral salt to the concentrates at a temperature higher than 18° C. and (b) precipitating the CIG from the supernatant using 12 to 33 w/v % of neutral salt. This process makes it possible to prepare factor VIII concentrates free of CIG and, alternatively, CIG, simultaneously from the same starting material.

The appropriate starting material is selected in dependence on a determination of the CIG, for example according to Mosesson and Umfleet, J. Biol. Chem. 245, 5728 (1979), of the factor VIII, for example according to Proctor, M. and Rapaport, O., Am. J. Clin. Path. 36, 212, (1961) and on that of the fibrinogen, for example according to Clauss, A., Acta haemat. 17, 237 (1957).

The process of the invention starts from factor VIII concentrates containing CIG, preferably from factor VIII concentrates poor in fibrinogen, and in particular from concentrates containing from 0 to 2 mg of fibrinogen/20 units of factor VIII.

Suitable factor VIII concentrates are plasma protein fractions enriched in factor VIII. They are obtainable, for example, by cryoprecipitation processes or by precipitation processes using amino acids and, if desired, they may be subjected to lyophilization.

For example, a lyophilized factor VIII concentrate can be dissolved in a 0.02–0.12M buffer, preferably citrate-NaCl buffer, of pH 6.0–8.0, preferably 6.9, in a concentration of from 0.2 to 20%, preferably 1%, referred to protein.

From 1.8 to 2.6 mols/l, preferably 2.2 mols/l, of a well water-soluble aliphatic amino acid, preferably glycine, and from 8 to 12%, preferably 12 w/v %, of neutral salt, preferably NaCl, in a solid state are added to the resulting solution at a temperature above 18° C., preferably at a temperature between 20° C. and 25° C. since denaturation occurs at rather high temperatures. The precipitate is separated, preferably by centrifugation, and, if desired, it may be used for the factor VIII preparation.

By adding neutral salt, the salt content of the supernatant is adjusted to a level between approximately 12 and 33 w/v %, preferably 17 w/v %. Suitable neutral salts are ammonium sulfate or, preferably, alkali metal halides which are sufficiently soluble in water.

The precipitate is obtained in the manner specified above. For further enrichment, the precipitate can be redissolved in a buffer solution the quantity of which is the same as or less than that of the starting volume, preferably a solution of the citrate buffer mentioned above. The precipitation process can subsequently be repeated.

Depending on the desired purity of the product, this precipitation step can be repeated several times or alternatively can be omitted. The final product should have a content of CIG of at least 60%, calculated on protein, and it should be free from protein coagulable with thrombin.

The final product is tested for accompanying gamma-globulin and fibrinogen with the acid of current protein-analytical methods such as polyacryloamide electrophoresis or immunoelectrophoresis using standards or specific antisera.

CIG is a valuable medicament. It is suitable especially for the shock therapy. This can be proved experimentally by the following three reactions in animals:

(a) the passive-cutaneous anaphylaxis reaction in the guinea pig;

(b) the endotoxin shock induced by lipopolysaccharides in the cat;

(c) the histamine shock in the guinea pig.

When administered prior to or after the shock induction at a dose of 10 mg/kg, CIG can reduce the shock effect. The dose of histamine or endotoxin required for inducing the shock is approximately 3 times that of the control.

For use as a medicament, the CIG is brought in known manner into a dosage form suitable for parenteral, preferably intravenous, administration. To this end, it is present in a concentration of approximately 10 mg/ml in aqueous solution or in dried, preferably lyophilized form. Appropriate additives such as carbohydrates, amino acids well soluble in water, and buffer salts such as glucose, glycine and sodium citrate, may be used for stabilizing the CIG activity. The preparation is also suitable for improving the opsonizing activity of phagocytizing cells.

The following example illustrates the invention:

EXAMPLE

Factor VIII concentrate poor in fibrinogen which has been obtained according to K. M. Brinkhous et al., JAMA, 205, 67 (1968) or according to M. Wickerhauser, Vox. Sang., 23, 402 (1972), is dissolved in a citrate-NaCl buffer, of pH 6.9 and containing the components in a quantity of 0.02 or 0.06 mol/l, to give a 1% solution, referred to protein. While stirring there are added batchwise at +22° C. 2.2 mols/l of glycine and subsequently 12 w/v % of NaCl, in solid state. Stirring is continued at this temperature for 2 hours and the precipitate is subsequently collected by centrifugation for 30 minutes at 3000 g. The precipitate can be further processed as factor VIII concentrate.

The supernatant is heated to +37° C. Solid NaCl is added thereto, while stirring, until a concentration of 17 w/v % is reached. Stirring is continued for 30 minutes at +37° C. and the precipitate is collected by centrifugation at 3000 g for 30 minutes. The supernatant is discarded.

The precipitate is dissolved in one-fourth the volume of the originally used citrate-NaCl buffer and again heated to 37° C. 2.2 mols/l of glycine and 17 w/v % of NaCl are added and the precipitate is again subjected to centrifugation.

The resulting precipitate is redissolved in one-tenth of the originally used volume of the citrate-NaCl buffer and dialyzed for 3 hours against 30 times the volume of this buffer. The solution is heated to 30° C. and subsequently subjected to centrifugation for 60 minutes at 3000 g to clarify.

The CIG-containing supernatant is diluted with citrate-NaCl buffer to a concentration of 1%, calculated on protein, 5 w/v % of glucose are added, the product is filtered under sterile conditions and lyophilized.

What is claimed is:

1. A method for isolating the cold insoluble globulin (CIG) from a blood plasma concentrate of factor VIII containing CIG, which method comprises adding from 1.8 to 2.6 mols per liter of a well water-soluble amino acid and from 8 to 12 weight/volume percent of a neutral salt to said concentrate at a temperature above 18° C. whereby a precipitate forms, separating the supernatant from the resulting precipitate, and increasing the concentration of neutral salt in the supernatant to precipitate the CIG.

2. A method as in claim 1, wherein said amino acid is glycine.

3. A method as in claim 1, which additionally comprises redissolving the CIG precipitate obtained in a buffer solution and adding from 1.8 to 2.6 mols per liter of a well water-soluble amino acid and from 8 to 12 weight/volume percent of a neutral salt to said solution, whereby a precipitate forms, separating the supernatant from the resulting pecipitate, and increasing the concentration of neutral salt in the supernatant to precipitate purified CIG.

* * * * *